United States Patent [19]

Taylor et al.

[11] Patent Number: 5,003,989
[45] Date of Patent: Apr. 2, 1991

[54] STEERABLE DILATION CATHETER

[75] Inventors: Charles S. Taylor, San Francisco; Hilary J. Hampton, Santa Clara, both of Calif.

[73] Assignee: Advanced Cardiovascular Systems, Inc., Santa Clara, Calif.

[21] Appl. No.: 550,530

[22] Filed: Jul. 10, 1990

Related U.S. Application Data

[62] Division of Ser. No. 350,580, May 11, 1989, Pat. No. 4,955,384.

[51] Int. Cl.⁵ .............................................. A61B 5/00
[52] U.S. Cl. ...................................... 128/772; 604/96; 604/280
[58] Field of Search ............................. 128/657, 772; 604/95–98, 164, 170, 280, 282

[56] References Cited

U.S. PATENT DOCUMENTS

| | | | |
|---|---|---|---|
| 3,674,014 | 7/1972 | Tillander | 128/657 |
| 4,723,936 | 2/1988 | Buchbinder et al. | 128/657 |
| 4,787,399 | 11/1988 | Bonello et al. | 128/657 |

Primary Examiner—Randall L. Green
Assistant Examiner—Randy Shay
Attorney, Agent, or Firm—Fulwider, Patton, Lee & Utecht

[57] ABSTRACT

A guidewire or guiding element for vascular catheters, particularly balloon dilation catheters having an elongated core member with a tapered distal portion with a flexible length of interfitting links on the tapered distal portion. The individual links generally comprise a base with an aperture therein and a plurality of upwardly extending arms with the ends of the arms bent inwardly toward the longitudinal axis of the flexible length to engage the base of an adjacent link. Improved flexibility and torquability are provided by the flexible length of interfitting links.

13 Claims, 4 Drawing Sheets

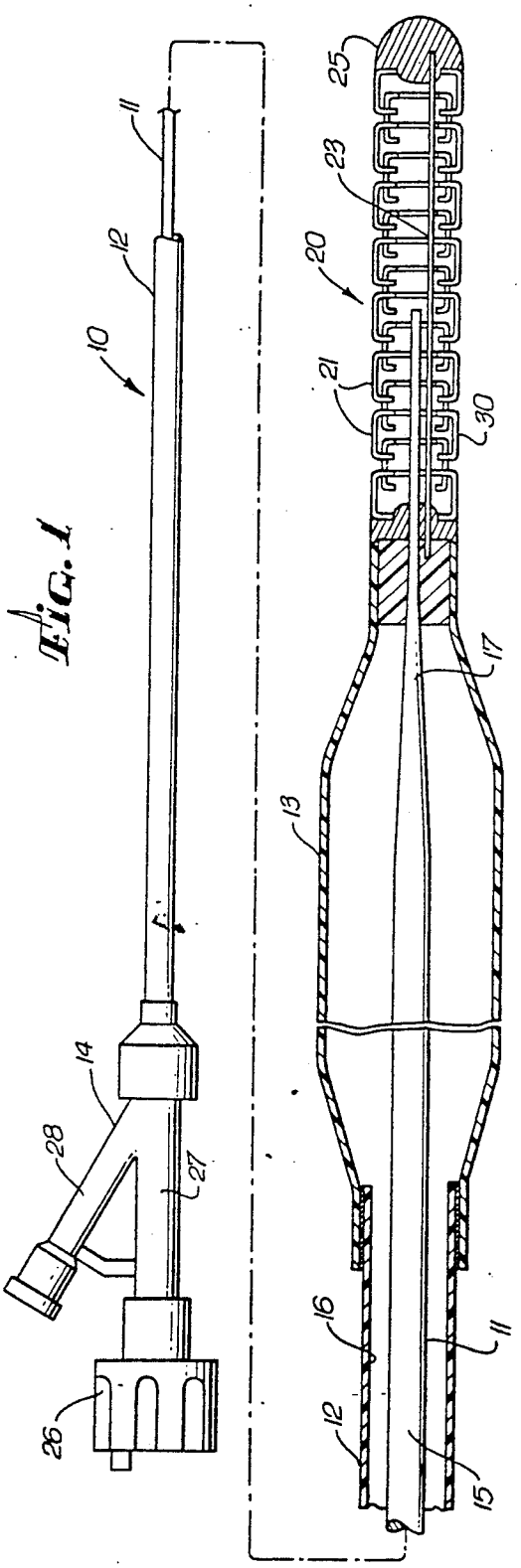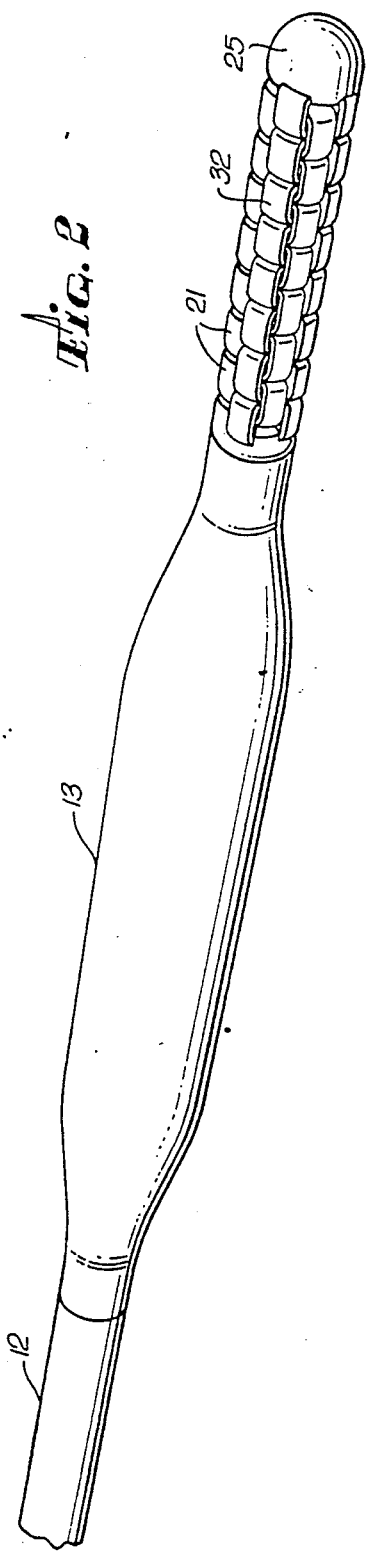

STEERABLE DILATION CATHETER

This is a division of application Ser. No. 350,580, filed May 11, 1989, now U.S. Pat. No. 4,955,384.

BACKGROUND OF THE INVENTION

This invention generally relates to guiding members for vascular catheters useful in such procedures as angiography, angioplasty, valvuloplasty and the like.

In typical percutaneous transluminal coronary angioplasty (PTCA) procedures, a guiding catheter having a preformed distal tip is percutaneously introduced into the cardiovascular system of a patient through the brachial or femoral arteries and advanced therein until the distal tip thereof is in the ostium of the desired coronary artery. A guidewire and a dilatation catheter having a balloon on the distal end thereof are introduced through the guiding catheter with the guidewire slidably disposed within an inner lumen of the dilatation catheter. The guidewire is first advanced into the patient's coronary vasculature until the distal end thereof crosses the lesion to be dilated and then the dilatation catheter is advanced over the previously introduced guidewire until the dilatation balloon is properly positioned across the lesion. Once in position across the lesion, the flexible, relatively inelastic balloon is inflated to radially compress atherosclerotic plaque against the inside of the artery wall to thereby dilate the lumen of the artery. The balloon is then deflated so that the dilatation catheter and the guidewire can be removed and blood flow resumed through the dilated artery.

Guidewires for vascular use usually comprise an elongated core member which is tapered toward the distal end, a helical coil disposed about and secured to the tapered distal end of the core member and a rounded plug provided on the distal tip of the coil. Preferably, the plug and at least part of the coil are formed of highly radiopaque materials to facilitate fluoroscopic observation thereof. There are two general types of guidewire constructions. In the first type, the core member extends through the coil to the plug in the distal tip thereof. In the second type, the core member extends into the interior of the helical coil, but terminates short of the plug in the distal tip. A shaping ribbon is secured directly or indirectly to the core member and the ribbon is secured to the radiopaque plug as shown.

Steerable dilatation catheters with built-in or fixed guidewires or guiding elements are used with greater frequency because the deflated profile of such catheters is generally smaller than conventional dilatation catheters with movable guidewires or elements having the same inflated balloon size.

Further details of angioplasty procedures and the devices used in such procedures can be found in U.S. Pat. No. 4,332,254 (Lundquist); U.S. Pat. No. 4,323,071 (Simpson-Robert); U.S. Pat. No. 4,439,185 (Lundquist); U.S. Pat. No. 4,468,224 (Enzmann et al.) U.S. Pat. No. 4,516,972 (Samson); U.S. Pat. No. 4,538,622 (Samson et al.); U.S. Pat. No. 4,554,929 (Samson et al.); and U.S. Pat. No. 4,616,652 (Simpson). Each of the above references is incorporated herein in their entirety.

Further details about guidewires can be found in U.S. Pat. No. 4,538,622 (Samson et al.); U.S. Pat. No. 4,554,929 (Samson et al.) U.S. Pat. No. 4,619,274 (Morrison); and U.S. Pat. No. 4,721,117 (Mar et al.).

Further details of low-profile steerable dilatation catheters may be found in U.S. Pat. No. 4,582,181 (Samson); U.S. Pat. No. 4,619,263 (Frisbie et al.); U.S. Pat. No. 4,641,654 (Samson et al.); and U.S. Pat. No. 4,664,113 (Frisbie et al.).

While the prior guidewires and guide members have for the most part performed well, there was always a need for increased flexibility and the increased torquability and pushability of the distal tip of the guidewire. With the prior devices, improvements in flexibility usually involved some loss of torquability and improvements in torquability usually involved some loss in flexibility. What has been needed and heretofore unavailable is some means to improve both the flexibility and torquability of the distal tip of the guidewire. The present invention satisfies that need.

SUMMARY OF THE INVENTION

This invention is directed to a guidewire or guiding member design having both improved flexibility and torquability, particularly in the distal portion thereof.

The guiding member of the invention generally includes an elongated core member which preferably tapers toward the distal end thereof. A plurality of interfitting links are provided on the distal portion of the core member to facilitate improvements in flexibility and torquability. Means are provided on the proximal end of the core member to apply torque thereto which is transmitted through the core member to the distal portion thereof having a section of loosely interfitting links.

In a presently preferred embodiment, the links comprise a relatively flat base and a plurality of vertically extending arms which fold inwardly in the upper portion thereof to engage the upper surface of the flat base of the adjacent link, with the length of the upwardly extending portion of the arms being chosen to provide a desirable amount of axial movement between the links. An opening, preferably centered, may be provided in the flat base of the link to receive the distal portion of the core member or a shaping ribbon which extends from the distal end of the core member to the distal tip of the flexible link section with a rounded plug formed in the distal end thereof.

The ends of the arms which extend upwardly from the flat base and are bent inwardly between the arms of the adjacent link are preferably provided with an enlargement on the end thereof for interlocking the links and to thereby prevent their separation, particularly during vascular procedures. Lost motion or winding between the individual links can be minimized by minimizing the spacing between the interfitting arms of the links.

The length of the interfitting links generally will assume the shape imposed on the shaping member or the distal end of the core which passes through the opening provided in the flat bases of the links.

These and other advantages of the invention will become more apparent from the following detailed description thereof when taken in conjunction with the accompanying exemplary drawings.

BRIEF DESCRIPTION OF THE DRAWINGS

FIG. 1 is an elevation view partially in section of a steerable, fixed wire dilatation catheter embodying features of the invention;

FIG. 2 is a perspective view of the distal portion of the dilatation catheter shown in FIG. 1;

DETAILED DESCRIPTION OF THE INVENTION

Figure 3:
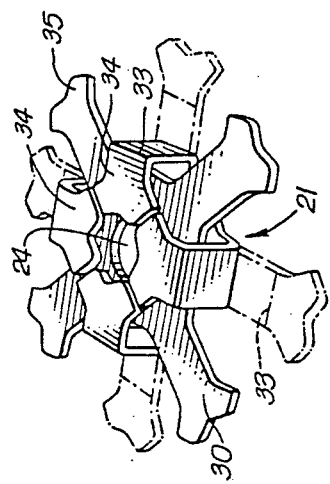
FIG. 3 is a perspective view of a link of a preferred embodiment.

Reference is made to FIGS. 1 and 2 which illustrate a steerable dilatation catheter assembly 10 having a fixed guidewire or guiding member 11 therein embodying features of the invention. The catheter assembly 10 generally comprises an elongated tubular body 12 having a balloon member 13 on the distal portion thereof adjacent the distal end and a multi-arm adapter 14 on the proximal end of the tubular body 12. A core member 15 is disposed within an inner lumen 16 provided within the tubular body 12 with a tapered distal portion 17.

A flexible section 20 of the catheter 10 includes a plurality of interfitting links 21 or is secured to the core member 15 at location 22 by means of welding, brazing, soldering, adhesives and the like. A shaping member or ribbon 23 extends through aperture 24 provided in the links 21 from the bond location 22 which secures the proximal end of the shaping member 23 to the core member 15 to the rounded plug 25 provided on the distal tip of the flexible link section 20.

A torquing knob 26 is provided on the proximal end of the core member 15 in a conventional fashion to allow the manual rotation of the guiding member or guidewire 11 in a desired manner to guide the catheter assembly 10 through a patient's vasculature. The two-arm adapter 27 on the proximal end of tubular member 12 has an arm 28 for injecting inflation fluid through the lumen 16 to the interior of balloon 13.

Figure 4:
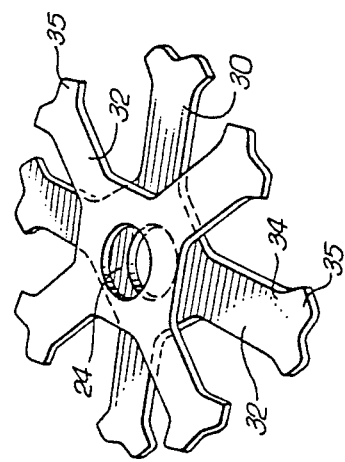
FIGS. 4 and 5 illustrate the interfitting of the links, such as shown in FIG. 3 to form the distal portion of the guiding member shown in FIGS. 1 and 2.
Figure 5:
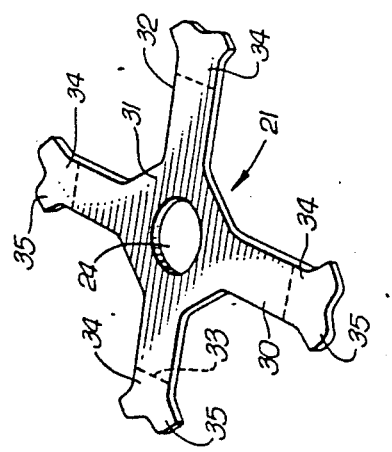

A preform 30 from which an individual link 21 can be made is shown in FIG. 3. As indicated, the preform 30 includes a base 31, preferably flat, having an aperture 24 and a plurality of projecting arms 32 extending radially outwardly from the base 31. However, as shown in FIGS. 4 and 5, the individual links 21 are interfitted by first placing one preform 30 on top of another, radially offsetting the upper preform so that the arms 32 of one of the preforms extend between the arms of the adjacent preform, as shown. The arms 32 of the lower preform 30 are folded upwardly at the junction thereof with the base 31 and then are folded inwardly again at an intermediate location 33, as shown in FIG. 5, so that the inwardly folded section 34 of the arms 32 limits the maximum axial displacement between adjacent links. Additional preforms are added in the same manner in order to form the flexible link section 20. The ends 35 of the inwardly folded arm section 32 are enlarged, preferably flaring outwardly, as shown, so that when the arm sections 34 are folded inwardly the links 21 interlock to thereby prevent the separation thereof during vascular procedures. The transverse dimension (i.e., the width) of the arms 32 controls the amount of relative axial rotation between adjacent links. The larger the width dimension, the less relative axial rotation is allowed between links 21 and thus the less lost motion from the proximal to the distal end of the flexible link section 20. The length of the shaping ribbon 23 extending between the bonding location 22 and the plug 25 at the distal tip of the flexible section 20 can determine the relative axial placement of the individual links 21 within the displacement allowed by the arms 32 of each link 21.

Figure 6:
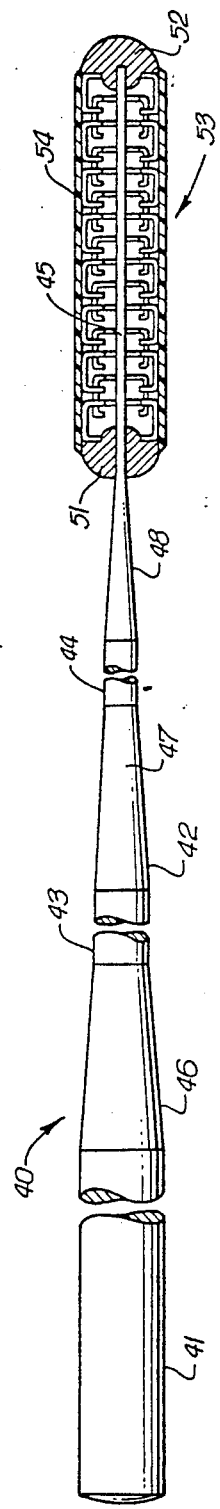
FIG. 6 is a side elevation view of a guidewire embodying features of the invention.

FIG. 6 illustrates another embodiment of the invention involving a movable guidewire 40 for use within the inner lumen of a dilatation catheter, not shown. The guidewire 40 generally comprises a relatively thin core 41 with a short tapered distal portion 42. All or a substantial part of the guidewire 40 may be provided with a thin Teflon coating (not shown) of about 0.0005 to about 0.001 inch (0.013 to 0.025 mm) to facilitate the passage thereof through the central lumen of the dilatation catheter. The tapered distal portion 42 has two sections 43-45 of progressively smaller cross-sectional dimensions with gentle tapers 46-48 between the progressively smaller sections. This embodiment has a standard design wherein section 45 extends to the plug 52 and is flattened to allow shaping. A flexible link section 53 is disposed about the short tapered distal portion 42 of the guidewire 40. The proximal end of the section 53 is secured to the distal portion 42 by welding, brazing, soldering, or adhesive at location 51. The distal end of the flexible link section 53 is secured to the plug 52. If desired, the entire length of the link section 53 may be covered by a flexible protective sheath 54, such as rubber, elastomer or the like. The distal end of the core 41 could be provided with a distal section, as shown in FIG. 1, if desired. The link section 53 typically has a length from about 1 to about 3 cm and in one presently preferred embodiment, at least some of the links are fabricated from a sheet of radiopaque material, such as molybdenum, rhenium, palladium, platinum, tungsten, and alloys thereof to make the link section more visible under fluoroscopic examination. Alloys of molybdenum and rhenium have been found to be particularly suitable with a nominal composition of 50 percent molybdenum and 50 percent rhenium being preferred. The links may also be made of stainless steel and NITINOL.

Figure 7:
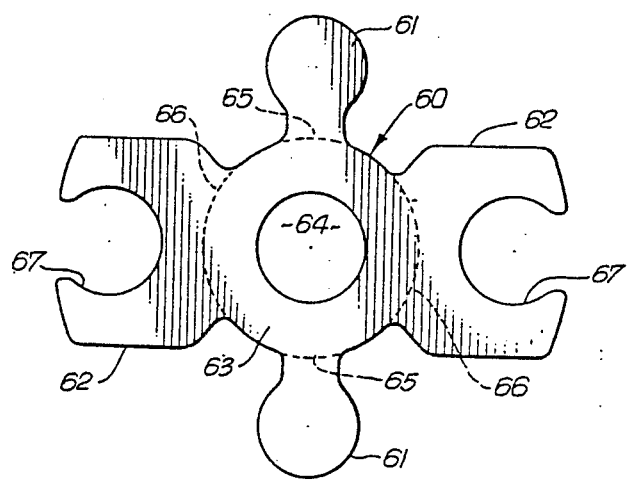
FIG. 7 is a plan view of an alternative link preform.
Figure 8:
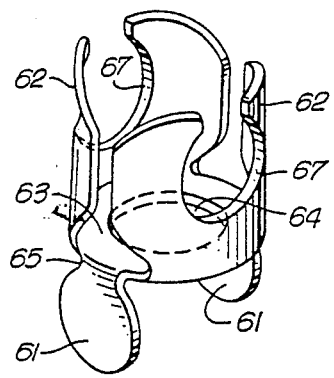
FIG. 8 is a perspective view of the link preform shown in FIG. 7 finally formed.
Figure 9:
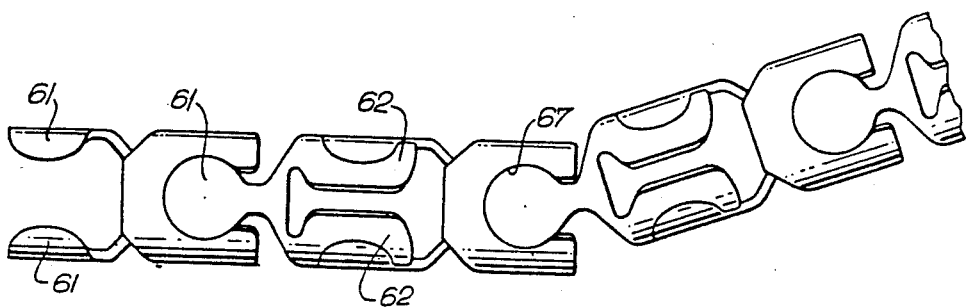
FIG. 9 is an elevation view of several links as shown in FIGS. 7 and 8 in an assembled condition.

An alternative link embodiment is illustrated in FIGS. 7-9. The link preform 60, best shown in FIG. 7, has a pair of opposing discs 61 and a pair of opposing socket sections 62 which are secured to the base 63 which has an aperture 64 therein which is adapted to receive a guiding element (not shown). As depicted in FIGS. 8 and 9, the discs 61 are bent along lines 65 in one axial direction and the socket sections 62 are bent along lines 66 in an axial direction opposite to that of the discs 61. The discs 61 of one link interfit the recess or socket 67 in an axially adjacent link which, as shown in FIG. 9, allows limited movement between the links, yet facilitates the transmission of torque between the links. Preferably, the socket sections 62 and the discs 61 are curved so as to form a generally cylindrical shape.

Figure 10:
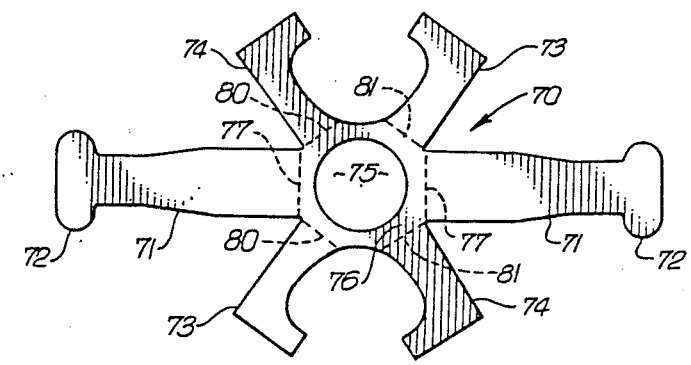
FIG. 10 is a plan view of an alternative link preform.
Figure 11:
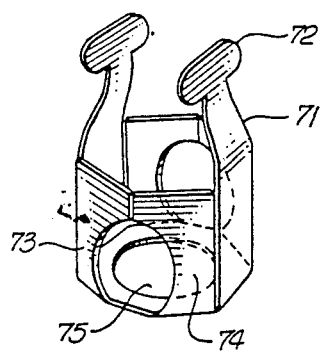
FIG. 11 is a perspective view of the link preform shown in FIG. 10.
Figure 12:
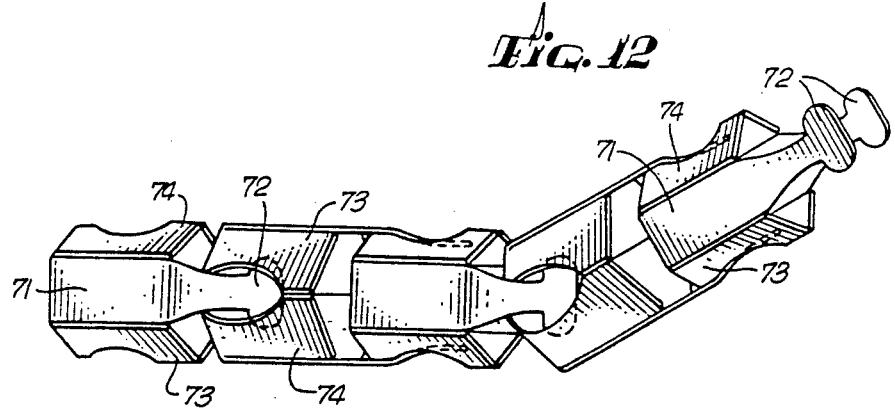
FIG. 12 is an elevation view of several links in an assembled condition.

FIGS. 10-12 illustrate another alternative link design which is suitable for use in the present invention. The link preform 70 is best shown in FIG. 10, whereas the forming and operation of the links are best shown in FIGS. 11 and 12. The preform 70 has a pair of opposing arms 71 which have rounded enlarged ends 72, a pair of opposing socket sections 73 and 74, and a central aperture 75 in the base 76 which is adapted to receive a guiding element (not shown). The arms 71 are bent axially in one direction at fold lines 77 and socket sections 73 and 74 are bent in the same axial direction along fold lines 80 and 81, as shown in FIG. 11. The distal tip of the arms 71 are bent inwardly, as shown in FIG. 11, so as to fit within the socket 82 of an adjacent link and be locked therein by the enlarged end 72 when the socket sections 73 and 74 are bent into their final positions. This construction allows pivotal movement between the links as in the previously described embodiments and provides for the transmission of torque between the links.

Generally, the size and materials of construction for the guidewire or guide element may be conventional, except as noted otherwise. Modifications and improvements can be made to the invention without departing from the scope thereof.

What is claimed is:

1. A steerable dilatation catheter comprising:
   (a) a tubular body having an inner lumen extending therein for delivery of inflation fluid therethrough;
   (b) an inflatable balloon on a distal portion of the tubular body adjacent a distal end thereof and in fluid communication with the inner lumen of the tubular body;
   (c) a core member extending through the interior of the balloon and out the distal end thereof; and
   (d) a flexible length of interfitting links disposed about and secured to the portion of the core member extending out of the distal end of the balloon.

2. The steerable catheter of claim 1 wherein a core member tapers in the distal portion thereof.

3. The steerable catheter of claim 1 wherein a rounded plug is formed at the distal tip of the flexible length of interfitting links.

4. The steerable catheter of claim 1 wherein the links are formed from a material selected from the group consisting of molybdenum, rhenium, stainless steel, nitinol, platinum, palladium, tungsten, and alloys thereof.

5. The steerable catheter of claim 1 wherein the flexible length of interfitting links is covered by a flexible sheath.

6. The steerable catheter of claim 1 wherein the individual links have at least three arms extending perpendicularly from a base of the link.

7. The steerable catheter of claim 1 wherein the links generally comprise a base having an aperture therein, a plurality of arms secured to the edge of the base with enlarged ends which form a socket, and a plurality of circular discs secured to the edge of the base, each of said discs being rotatedly disposed within a socket formed by the arms of an adjacent link.

8. The steerable catheter of claim 1 wherein the links have a base with an aperture and a plurality of arms which extend from the base and which have means to engage an adjacent link.

9. The steerable catheter of claim 8 wherein the arms which extend from the link bases have free ends which are folded inwardly to engage the base of an adjacent link.

10. The steerable catheter of claim 9 wherein the inwardly folded free end of the free ends have enlarged tips.

11. The steerable catheter of claim 1 wherein the core member extends through apertures provided in bases of the links.

12. The steerable catheter of claim 11 wherein a shaping member having proximal and distal ends is secured by its proximal end to the core member, extends through the apertures of a plurality of links and is secured by its distal end to a plug at the distal end of the length of the links.

13. The steerable catheter of claim 1 wherein means are provided to secure both ends of the flexible length of interfitting links to the core member.

* * * * *